United States Patent [19]

Bernstein

[11] Patent Number: 4,536,404
[45] Date of Patent: Aug. 20, 1985

[54] METHOD AND COMPOSITION FOR TREATING POST-HERPETIC NEURALGIA

[75] Inventor: Joel E. Bernstein, Deerfield, Ill.

[73] Assignee: Dermatological Enterprises, Ltd., Northbrook, Ill.

[21] Appl. No.: 504,963

[22] Filed: Jun. 16, 1983

[51] Int. Cl.³ .................... A61K 31/165; A61K 35/78
[52] U.S. Cl. .................................. 514/627; 424/195.1
[58] Field of Search ................................ 424/195, 324

[56] References Cited

U.S. PATENT DOCUMENTS 3,880,996  4/1975  Fisher .................................. 424/184

Primary Examiner—Albert T. Meyers
Assistant Examiner—John W. Rollins, Jr.
Attorney, Agent, or Firm—Ronald A. Sandler; Jerry A. Schulman

[57] ABSTRACT

The invention relates to a method of treating herpes zoster in a patient having herpes zoster wherein an effective amount of capsaicin is topically applied to the area affected with herpes zoster for a time sufficient to relieve the symptoms thereof.

7 Claims, No Drawings

METHOD AND COMPOSITION FOR TREATING POST-HERPETIC NEURALGIA

BACKGROUND OF THE INVENTION

Herpes zoster (shingles) is a recurrent form of infection with the varicella virus (chickenpox virus). The condition is characterized by pain and burning, followed by the appearance of grouped vesicles (blisters) in a dermatomal distribution. Although spontaneous resolution usually occurs in 2-3 weeks, in some cases, especially in the aged, severe pain termed post-herpetic neuralgia may ensue. Strong oral analgesics may be necessary to control this pain. While treating a psoriasis patient with the active principle in red pepper, the patient noted that not only the psoriatic lesions on her chest and side resolved, but that the post-herpetic stinging she had experienced on her right side disappeared. This surprising observation led me to evaluate the effectiveness of topically applied capsaicin, in a pharmaceutically acceptable carrier, in three other patients with chronic post-herpetic neuralgia.

SUMMARY OF THE INVENTION

It is an object of this invention to provide a method of treating herpes zoster in patients in need of such treatment. In conjunction with the above object, post-herpetic neuralgia is treated by repeated topical applications of capsaicin to the affected area.

DESCRIPTION OF THE PREFERRED EMBODIMENTS

EXAMPLE 1

A seventy-four year old woman with chronic post-herpetic neuralgia had been experiencing severe burning pain on her right side for almost two years. She was only poorly controlled on aspirin and codeine. The patient topically applied 0.1% capsaicin in a pharmaceutically acceptable cream vehicle to the painful area on her side four times a day. After two weeks, she was pain free and able to discontinue her oral analgesics. After six pain-free months of topically applying capsaicin, this patient was able to discontinue capsaicin treatment and she remained pain free.

EXAMPLE 2

A sixty-eight year old man experienced severe pain on his lower right side for over six months following an episode of herpes zoster. Daily topical applications of 0.1% capsaicin cream for two weeks provided significant reduction of this pain and after one month of topical treatment he was pain free in the previously excruciatingly painful area.

EXAMPLE 3

An eighty-three year old woman with severe post-herpetic pain on her chest, unrelieved by oral analgesics, applied 0.025% capsaicin cream to the skin four times daily for two weeks. At the end of this treatment period she was able to discontinue the use of all oral pain medications and sleep comfortably for the first time in months.

In the practice of the present invention, capsaicin is distributed according to known techniques in various pharmaceutically acceptable carriers such as emulsions, solutions, suspensions including lotions, creams and ointments. Some of these carriers contain volatile diluents such as alcohol, glycol and the like and also may contain wetting agents, emulsifying and suspending agents.

Capsaicin, the active ingredient in the preparation, is a pungent principle in fruit of the various species of Capsicum or Solanaceae (pepper plants). Chemically, Capsaicin is known as trans-8-methyl-N-vanillyl-6-nonenamide or (E)-N-[(4-hydroxy-3-methoxyphenyl)-methyl]-8-methyl-6-nonenamide. Its structure is:

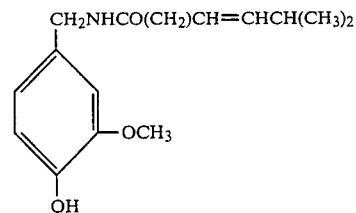

Capsaicin, commercially available from the Sigma Chemical Company, is preferably present in the pharmaceutically acceptable carrier in an amount of not less than 0.01% by weight and is preferably present in the range of from about 0.01% by weight to about 0.1% by weight, although higher concentrations may be used.

If capsaicin is present in the pharmaceutically acceptable carrier in an amount less than about 0.01% by weight, then there is insufficient concentration of the capsaicin to provide effective therapy. If the capsaicin is present in an amount substantially greater than about 1.0% by weight of the pharmaceutically acceptable carrier, then the topical application is too painful. Patients treated with capsaicin for psoriatic skin have initially experienced an intense red painful reaction (for the higher concentrations); however, the psoriatic skin becomes quite tolerant to capsaicin applications upon subsequent treatment. For patients with herpes zoster, the pain from the virus is so great that pain due to treatment with capsaicin has not been a significant problem, whereby higher concentrations may be applicable for treatment of herpes zoster than for psoriasis.

While there has been described what at present is considered to be the preferred embodiment of the present invention, it will be appreciated that various modifications and alterations may be made therein without departing from the true scope and spirit of the present invention, which the claims appended hereto are intended to cover.

I claim:

1. A method of treating post-herpetic neuralgia due to herpes zoster in a patient having herpes zoster comprising topically applying an effective amount of capsaicin in a pharmaceutically acceptable carrier to the area affected with herpes zoster for a time sufficient to relieve the symptoms of post-herpetic neuralgia due thereto.

2. The method of claim 1, wherein the capsaicin is applied at least daily.

3. The method of claim 1, wherein the capsaicin is applied more than once daily.

4. The method of claim 3, wherein the capsaicin is applied about four times daily.

5. The method of claim 1, wherein the capsaicin is present in an amount not less than about 0.01% by weight of the carrier.

6. The method of claim 1, wherein the capsaicin is present in an amount not greater than about 1% by weight of the carrier.

7. The method of claim 1, wherein the capsaicin is present in the range of from about 0.025% to about 0.1% by weight of the carrier.

* * * * *